US012533479B2

(12) United States Patent
Browne

(10) Patent No.: US 12,533,479 B2
(45) Date of Patent: Jan. 27, 2026

(54) POSITIVE AIRWAY PRESSURE MASK MONITOR

(71) Applicant: Jason Charles Browne, Portola Valley, CA (US)

(72) Inventor: Jason Charles Browne, Portola Valley, CA (US)

(73) Assignee: Jason Charles Browne, Portola Valley, CA (US)

( * ) Notice: Subject to any disclaimer, the term of this patent is extended or adjusted under 35 U.S.C. 154(b) by 1062 days.

(21) Appl. No.: 16/868,417

(22) Filed: May 6, 2020

(65) Prior Publication Data

US 2020/0353190 A1 Nov. 12, 2020

Related U.S. Application Data

(60) Provisional application No. 62/844,670, filed on May 7, 2019.

(51) Int. Cl.
*A61M 16/00* (2006.01)
*A61M 16/06* (2006.01)

(52) U.S. Cl.
CPC ........ *A61M 16/0051* (2013.01); *A61M 16/06* (2013.01); *A61M 2205/18* (2013.01); *A61M 2205/3584* (2013.01); *A61M 2205/52* (2013.01); *A61M 2205/582* (2013.01)

(58) Field of Classification Search
CPC .............. A61M 16/0051; A61M 16/06; A61M 2205/18; A61M 2205/3584; A61M 2205/52; A61M 2205/582
See application file for complete search history.

(56) References Cited

U.S. PATENT DOCUMENTS

| | | | | |
|---|---|---|---|---|
| 6,349,724 | B1 * | 2/2002 | Burton | F04D 25/166 128/204.18 |
| 10,589,051 | B2 * | 3/2020 | Salter | A61M 16/16 |
| 2005/0076906 | A1 * | 4/2005 | Johnson | A61M 16/024 128/204.21 |
| 2013/0118500 | A1 * | 5/2013 | Stevens | A61M 16/0051 128/205.25 |
| 2017/0196761 | A1 * | 7/2017 | Hyde | A61H 9/0057 |

* cited by examiner

*Primary Examiner* — Steven O Douglas

(57) ABSTRACT

The present invention teaches systems, devices, and methods to monitor the correct positioning of a positive airway pressure (PAP) mask. In the system, a PAP mask monitor is configured to capture sound from a PAP device over a first period of time; capture sound from a patient breathing over the first period of time; determine a difference between the PAP device sound and the patient breathing sound over the first period of time; and identify, based on a fast Fourier transform (FFT) analysis a selected frequency that can distinguish the patient's breathing from other noise. The PAP mask monitor is further configured to assert a dislodged mask alert signal if a breathing event is not detected during a determined apnea time window; and communicate an alarm signal to a smart wearable device that will awaken the patient so that the mask can be re-positioned properly.

18 Claims, 10 Drawing Sheets

30B

54

56

POSITIVE AIRWAY PRESSURE MASK MONITOR

BACKGROUND

Technical Field

The present disclosure generally relates to systems, devices, and methods associated with sleep apnea. More particularly, but not exclusively, the present disclosure relates to monitoring the correct placement of a continuous positive airway pressure (CPAP) mask.

Description of the Related Art

According to the World Health Organization, sleep apnea is a medical condition that affects up to 6% of adults and 2% of children. Generally, sleep apnea is a condition in which a patient's airway relaxes during sleep, and the patient's mouth or throat tissue partially or fully blocks the patient's airway. These blockages, which are called "apneas," interrupt breathing, raise blood pressure, cause snoring, lead to long-term fatigue, and tend to negatively affect the health and well-being of the sleep apnea sufferer.

Sleep apnea is conventionally treated with a positive airway pressure (PAP) machine. One device is a continuous positive airway pressure (CPAP) machine. A CPAP machine provides a continuous, steady flow of pressurized air to the patient. Another device is a bi-level positive airway pressure (BIPAP) machine. The BIPAP machine delivers two levels of positively pressurized air to the patient; a first pressure level is delivered when the patient inhales, and a second pressure level is delivered when the patient exhales. And a third device is an automatic positive airway pressure (APAP) machine. The APAP machine delivers air at a variable pressure calculated on a breath-by-breath basis. Other such positive airway machines are also contemplated.

The pressurized air of a PAP machine is delivered through flexible tubing to a mask, which is affixed to the patient's face when the patient sleeps. The amount of pressure in the air flow is generally prescribed by a medical practitioner and selected in the range of about 4 to about 30 centimeters of water pressure, which is typically abbreviated, "cm H2O" or "CWP."

A PAP machine is expensive, invasive, and typically uncomfortable for a patient to use. Nevertheless, a PAP machine remains the accepted form of non-surgical treatment currently available for sleep apnea sufferers. For this reason, PAP machines are in wide use.

The usefulness of a PAP machine to reduce or remove the dangerous effects of sleep apnea is based on the machine's ability to deliver pressurized air to the patient when the patient sleeps. If the pressurized air provided by the PAP machine leaks, then the ability of the PAP machine to remediate the effects of sleep apnea will be reduced or eliminated.

A leak in a PAP system can occur within the PAP machine, in a hose, at a sealed fitting, in the PAP mask, or through a breached seal between the mask and the patient's body. If the pressurized air leaks, then the ability of the PAP machine to remediate the effects of sleep apnea will be reduced or eliminated.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which, in and of itself, may also be inventive.

BRIEF SUMMARY

The following is a summary of the present disclosure to provide an introductory understanding of some features and context. This summary is not intended to identify key or critical elements of the present disclosure or to delineate the scope of the disclosure. This summary presents certain concepts of the present disclosure in a simplified form as a prelude to the more detailed description that is later presented.

The device, method, and system embodiments described in this disclosure (i.e., the teachings of this disclosure) include a device that monitors a positive airway pressure (PAP) mask for proper sealed placement on the skin of a sleep apnea patient over the patient's nose, mouth, or nose and mouth. The PAP mask monitor device works by analyzing data representing sound produced by a PAP device that provides the pressurized air to the PAP mask and determining whether or not the sleep apnea patient is performing regular breathing events or irregular breathing events. If the patient is performing irregular breathing events, the PAP mask monitor will communicate an alert signal to a smart wearable device being worn by the patient, and the smart wearable device will alert the patient using, for example, a tactile output such as a vibration. The vibration will be sufficient to wake the patient at least enough that the patient will rearrange the PAP mask into a properly sealed placement.

This Brief Summary has been provided to introduce certain concepts in a simplified form that are further described in detail below in the Detailed Description. Except where otherwise expressly stated, the Brief Summary does not identify key or essential features of the claimed subject matter, nor is it intended to limit the scope of the claimed subject matter.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIG. 16 is an updated sleep apnea environment in which the patient's PAP mask has been dislodged;

DETAILED DESCRIPTION

The present invention may be understood more readily by reference to this detailed description of the invention. The terminology used herein is for the purpose of describing specific embodiments only and is not limiting to the claims unless a court or accepted body of competent jurisdiction determines that such terminology is limiting. Unless specifically defined herein, the terminology used herein is to be given its traditional meaning as known in the relevant art.

Positive airway pressure (PAP) machines are a widely accepted form of non-surgical treatment for sleep apnea sufferers. These PAP machines, which include continuous positive airway pressure (CPAP) machines, bi-level positive airway pressure (BIPAP) machines, automatic positive airway pressure (APAP) machines, and other PAP machines, are expensive, invasive, and typically uncomfortable for a patient to use. Nevertheless, because of their effectiveness, they remain in wide use.

The usefulness of a PAP machine to reduce or remove the dangerous effects of sleep apnea is based on the machine's ability to deliver pressurized air to the patient when the patient sleeps. If the pressurized air provided by the PAP machine leaks, then the ability of the PAP machine to remediate the effects of sleep apnea will be reduced or eliminated.

A leak in a PAP system can occur within the PAP machine, in a hose, at a sealed fitting, in the PAP mask, or through a breached seal between the mask and the patient's body. If the pressurized air leaks, then the ability of the PAP machine to remediate the effects of sleep apnea will be reduced or eliminated. It has been recognized by the inventor that the most common types of leaks in a PAP system occur when the seal between the mask and the patient's body is breached, and this type of leak occurs most often when the patient dislodges their mask during sleep. Accordingly, a mechanism that can detect a dislodged PAP mask and alert the patient or some other practitioner would provide valuable health benefits to a patient with sleep apnea.

Figure 1A:
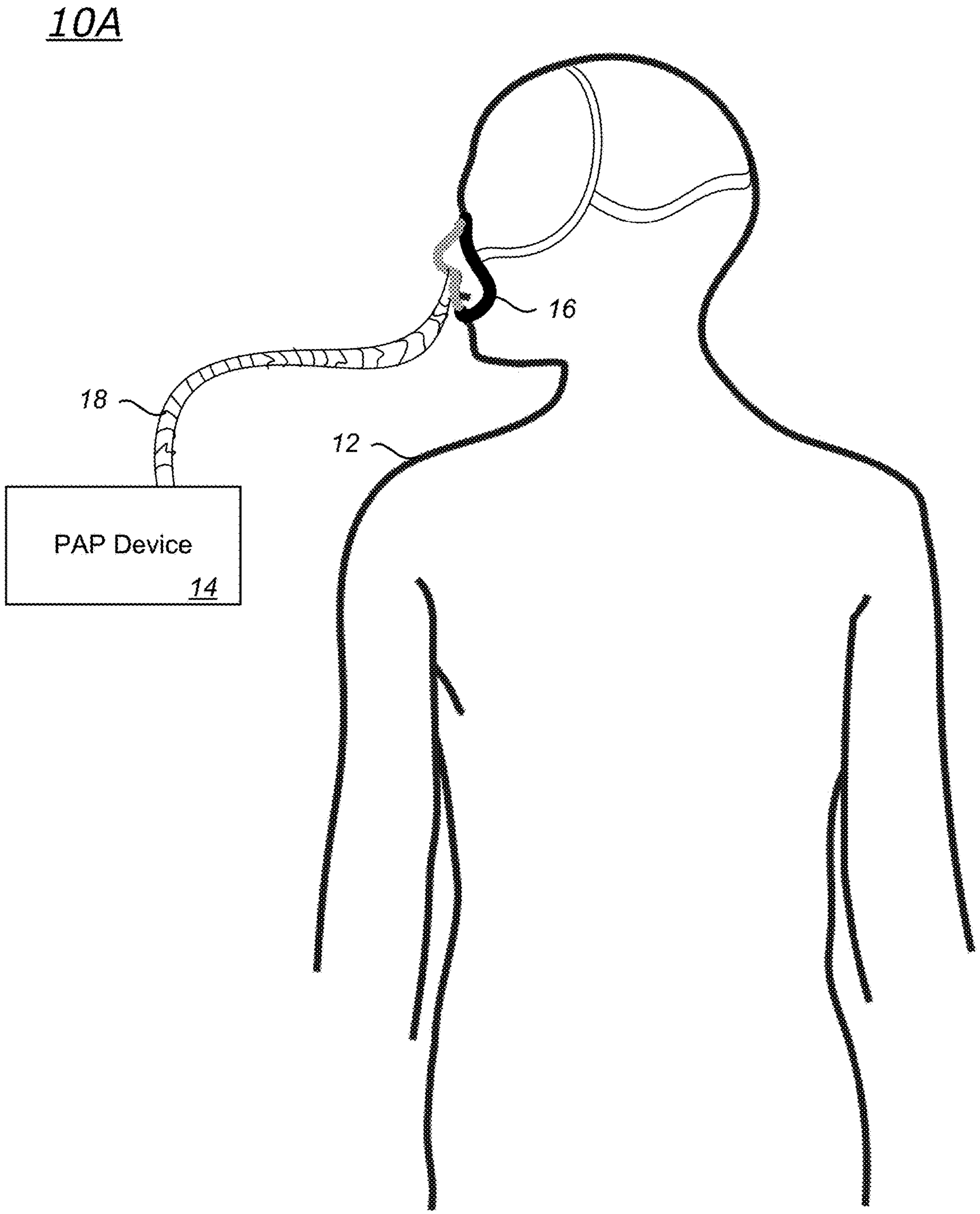
FIG. 1A is a sleep apnea environment embodiment.

FIG. 1A is a sleep apnea environment 10A. In the environment, a patient 12 is lying, on his back. A positive airway pressure (PAP) machine is providing a supply of pressurized air to a PAP mask 16 via a flexible hose 18.

Figure 1B:
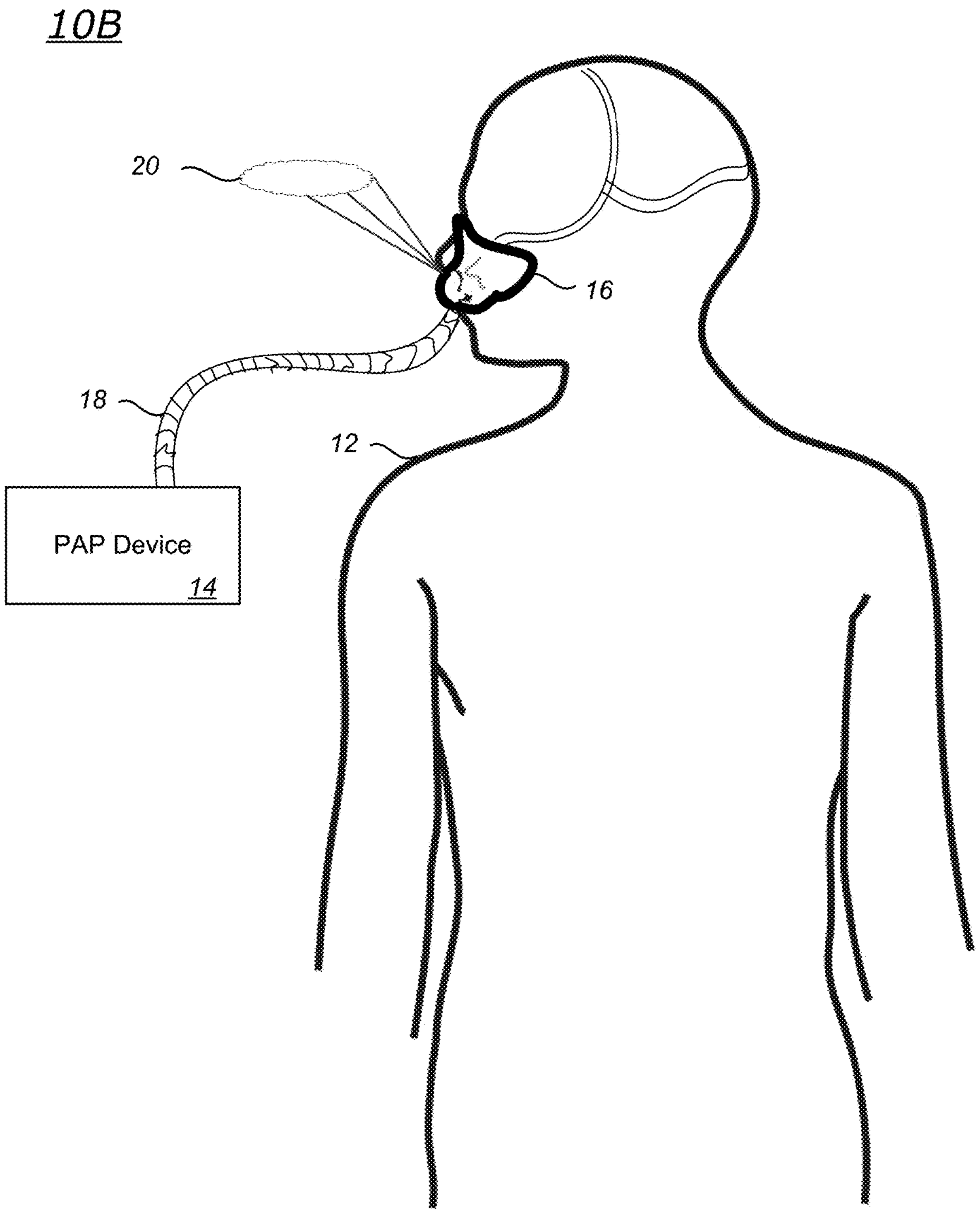

FIG. 1B is an updated sleep apnea environment 10B in which the patient's PAP mask has been dislodged. Structures earlier identified are not repeated for brevity. In the present disclosure, FIGS. 1A-1B may be collectively referred to as FIG. 1.

In FIG. 1B, pressurized air 20 is escaping from a breached seal in the PAP mask 16. The PAP mask 16 may have been knocked off or removed unconsciously, instinctively, accidentally, inadvertently, intentionally, unintentionally, or in some other way by the patient 12. The patient 12 remains asleep.

To address the problems caused by the undetected dislodge of the PAP mask, 16, the present inventors have created systems, devices, and methods (i.e., the teachings of the disclosure) to determine when a PAP mask has been dislodged and to gently alert the patient 12 so that that he can re-orient the PAP mask 16 in a sealed configuration.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems, including client and server computing systems as well as networks, have not been shown or described in detail to avoid unnecessarily obscuring descriptions of the embodiments.

Figure 2A:
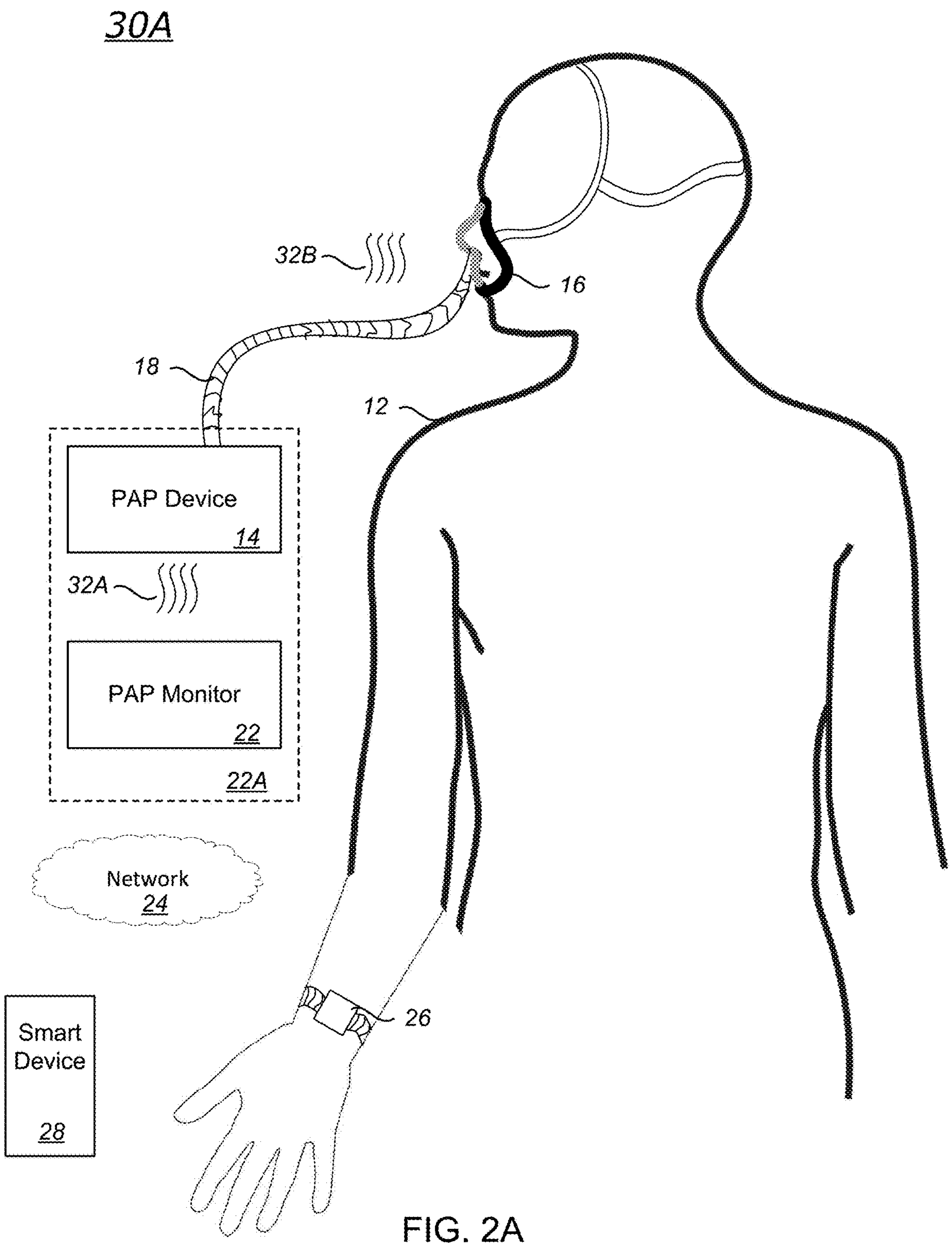
FIG. 2A is another sleep apnea environment embodiment.

FIG. 2A is another sleep apnea environment embodiment 30A. Structures earlier identified are not repeated for brevity. In the environment 30A of FIG. 2A, a PAP monitor 22 is located in the room where the patient 12 is sleeping. The PAP monitor 22 may be placed in proximity (e.g., within 12 inches, within 36 inches, within 120 inches) of the PAP device 14. A smart wearable device 26 is affixed to the patient 12, and the PAP monitor is arranged to communicate with the smart wearable device via a communications network 24. A smart device 28, which may be a mobile computing device (e.g., a smart phone, a tablet, or the like) may also be arranged to communicate with one or both of the PAP monitor 22 and the smart wearable 26. In at least one embodiment, the PAP monitor 22 is arranged to monitor noise 32A from the PAP device 14, noise 32B from the patient, and noise from any other source.

In at least some cases, the PAP monitor 22 and the PAP device 14 are integrated into the same combination PAP device 22A. The combination PAP device 22A in at least some cases may be formed as a PAP device 14 having a separate and distinct PAP monitor 22 inside the PAP device cabinet. In other cases, the combination PAP device 22A is a PAP device 22 having the functionality of the PAP monitor 22 "built in."

In other embodiments, a combination PAP device 22A can be implemented by integrating the mask removal alert technology of the present disclosure directly into a CPAP, BIPAP, ASV, or other sleep apnea technology machine. In at least some cases, a conventional PAP monitor 22 device may have sensors already in place to manage the air pressure in the patient's closed mask system. In some cases, based on information from these sensors, a conventional PAP monitor 22 may alert the patient with a low level beep when conditions indicate a certain pressure drop (e.g., when the mask is removed). This conventional alert system, however, is not desirable. If the low level beep is too quiet, the patient is not alerted, and if the low level beep is too loud, not only is the patient awoken, but so are others (e.g., human, pets, etc.) in the room or even in nearby rooms.

To remedy the shortcomings of the conventional systems, the combination PAP device 22A is arranged to detect mask removal based on data input from the existing pressure or other such sensors. By detecting changes to pressure in the mask, the combination PAP device 22A triggers an alarm by waking the patient through a wireless connection to the wearable device that will vibrate. The amount of vibration necessary to wake the patient may be user customizable by manual parameter data entry, programmatic data entry, or in some other way. In this way, the combination PAP device 22A can prevent others being disturbed when the PAP patient mask is dislodged. The manufacturers of known CPAP, BIPAP, ASV, and other sleep apnea technology devices have failed to devise this clever solution to an important problem that all such CPAP, BIPAP, ASV, and other sleep apnea technology devices have.

Figure 2B:
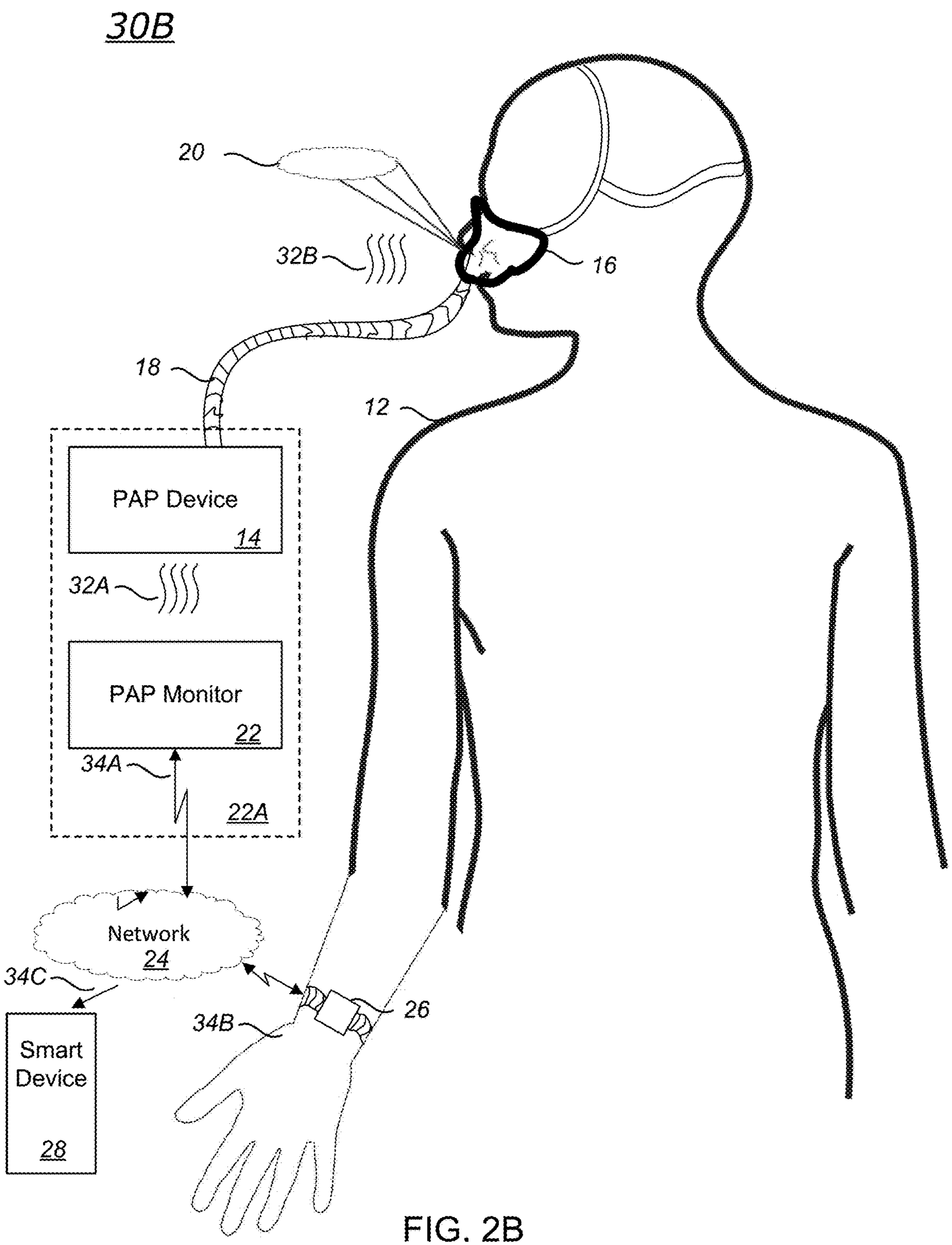
FIG. 2B is another updated sleep apnea environment in which the patient's PAP mask has been dislodged.

FIG. 2B is another updated sleep apnea environment 30B in which the patient's PAP mask 16 has been dislodged. Structures earlier identified are not repeated for brevity. In the present disclosure, FIGS. 2A-2B may be collectively referred to as FIG. 2.

In FIG. 2B, the PAP monitor 22 has determined that the patient's PAP mask 16 has been dislodged, and the PAP monitor 22 has communicated at least one signal to alert the patient 12. One or more signals 34A are communicated from the PAP monitor via communications network 24. Optionally, signals 34B are passed directly to the smart wearable 26, or optionally, signals 34C are passed to the smart device 28. When signals are passed to the smart device 28, corresponding signals 34B may also be communicated to the smart wearable 34B from either the PAP monitor 22 or the smart device 28. Communications 34A, 34B, 34C may desirably be arranged as unidirectional signals or bidirectional signals. Upon receiving the signal, the smart wearable will provide an alert (e.g., a tactile alert, an audio alert, a visible alert, or some other alert) to the patient 12.

Figure 3:
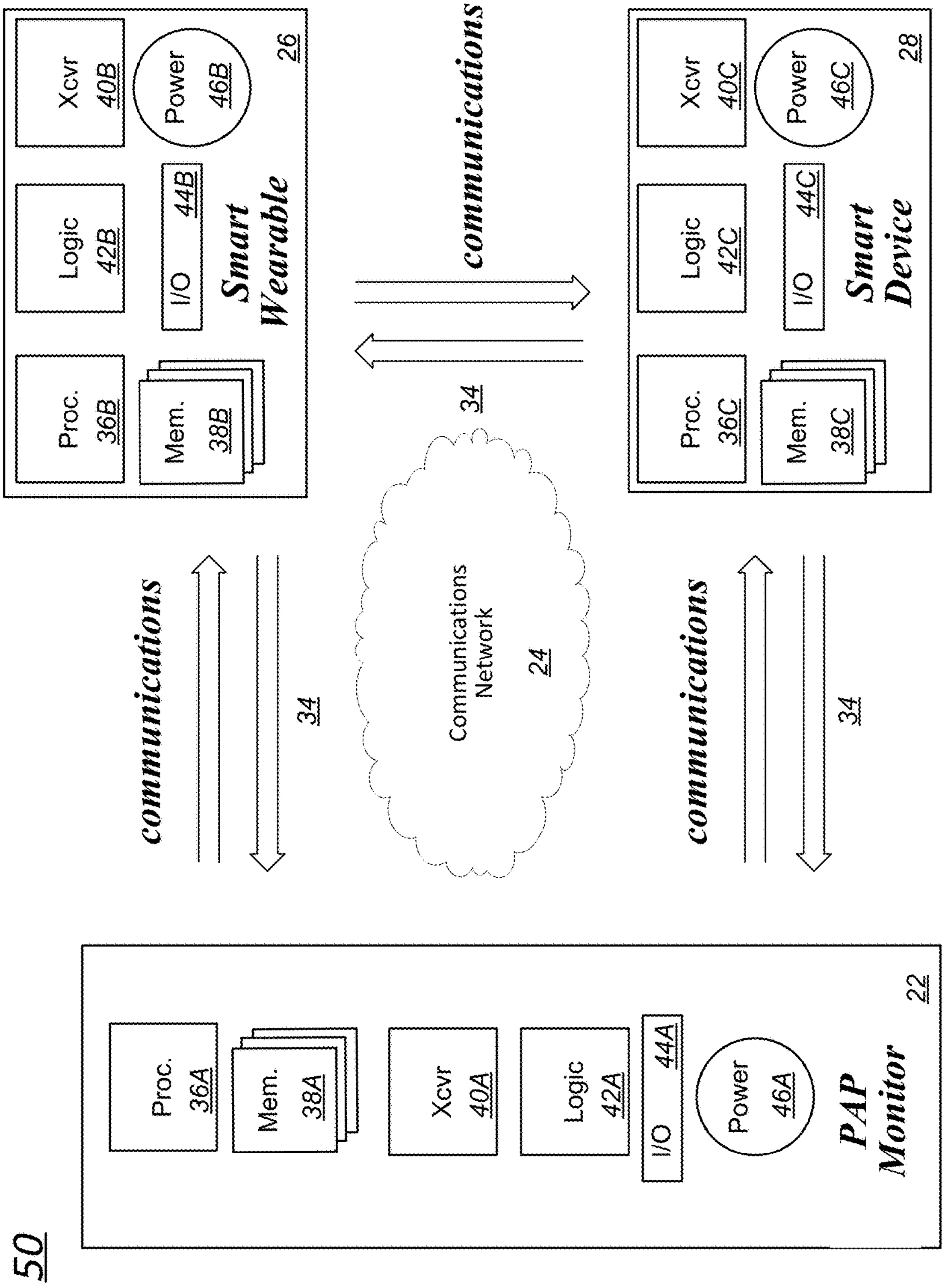
FIG. 3 is a sleep apnea system embodiment with several devices shown in more detail.

FIG. 3 is a sleep apnea system 50 embodiment with several devices shown in more detail. Each of the PAP monitor 22, smart wearable 26, and smart device 28 includes a processor 36A, 36B, 36C, respectively, one or more memory devices 38A, 38B, 38C, respectively, a transceiver 40A, 40B, 40C, respectively, a logic module 42A, 42B, 42C, respectively, an input/output (I/O) module 44A, 44B, 44C, respectively, and a power circuit 46A, 46B, 46C, respectively. It is recognized that the structures of each device may be different, and it is further recognized the processor-executable software instructions and memory stored in each device will be different. Nevertheless, one of skill in the art will recognize that such devices may be described with brevity so as to not obscure the inventive content described herein. Other operative components of the PAP monitor 22, smart wearable 26, and smart device 28 are not shown for brevity and to avoid obscuring the inventive teaching herein. The operative components of the PAP monitor 22, smart wearable 26, and smart device 28 are communicatively coupled (e.g., one or more address buses, data buses, and other such conduits that conform to any selected protocol) and electrically coupled (e.g., one or more power buses, power planes, and the like) as known by one of ordinary skill in the art.

In at least some cases, the respective processor 36A, 36B, 36C is a low power microcontroller and the one or more memory devices 38A, 38B, 38C include volatile memory (e.g., random access memory (RAM)) and non-volatile memory (e.g., read only memory (ROM), flash memory, or the like). In at least some cases, computer readable software instructions stored in the one or more memory devices 38A, 38B, 38C are executed by the respective processor 36A, 36B, 36C to carry out the functions of the PAP monitor 22, smart wearable 26, and smart device 28 as the case may be.

The respective logic module 42A, 42B, 42C may include any selected logic. In some cases, any one or more of the logic modules 42A, 42B, 42C are arranged to include at least one micro-electromechanical system (MEMs) device. In these cases, the MEMs device may include one or more of a plurality of MEMs devices drawn from a group that includes one or more of an accelerometer, a microphone, a motion sensor, a gyroscope, a pressure sensor, a thermal actuator, a magnetic actuator, a high aspect electrostatic resonator, a comb-drive, or some other MEMs structures. In the alternative, or in addition, any one or more of the logic modules 42A, 42B, 42C may include a motor (e.g., a vibration device), an audio device (e.g., a piezoelectric device, a speaker, or the like), a presentation device such as one or more light emitting diodes or a display, or some other type of logic.

The transceivers 40A, 40B, 40C in at least some embodiments are arranged for wireless, bidirectional communications with at least one other computing device. Communications 34 in FIG. 3 represent unidirectional, bidirectional, or multi-directional communications via any suitable wired or wireless protocol via a communications network 24.

The power circuit 46A, 46B, 46C, in any or all of the PAP monitor 22, smart wearable 26, and smart device 28 may in some cases be arranged as battery. The battery may supply any needed current at any determined voltage. In at least one case, the power circuit 46A, 46B, 46C, is arranged to provide between 1.6 VDC and 3.0 VDC at 200 milliAmp hours (200 mAH). In other embodiments, the power circuit 46A, 46B, 46C, will provide power at some other parameters (e.g., voltage, current, time). The power circuit 46A, 46B, 46C may include a rechargeable battery, a non-rechargeable battery, a capacitor, or some other storage device. The power circuit 46A, 46B, 46C may be arranged as a recharge circuit electronically coupled to a power storage device. In addition, or in the alternative, the respective power circuit 46A, 46B, 46C is arranged to deliver power to the processor, memory, logic, transceiver, and other circuits of the PAP monitor 22, smart wearable 26, and smart device 28. In at least one case, the power circuit 46A, 46B, 46C includes an induction circuit arranged to receive a wireless power signal and further arranged to charge a power storage device based on the received wireless power signal.

In at least some cases, an I/O module 44A, 44B, 44C will include a port that works cooperatively with a respective power circuit 46A, 46B, 46C and power storage device. In these and other cases, such an I/O port may be used to pass a wired power supply signal into the PAP monitor 22, smart wearable 26, and smart device 28, and the wired power supply signal can be used to charge the power storage device (e.g., a battery). In some cases, the I/O port may be used to: 1) pass information to the device, 2) pass information from the device, or 3) pass information both to and from the device. The I/O module 44A, 44B, 44C, via such an I/O port may communicate via a single wire protocol (SWP), a multi wire protocol (e.g., USB), or via some other protocol and communication medium. In at least some cases, the I/O port is useful for retrieving PAP mask data from the respective PAP monitor 22, smart wearable 26, and smart device 28.

The I/O module 44A, 44B, 44C may be used in other ways in some embodiments. For example, in at least some cases, the I/O module 44A, 44B, 44C is useful for uploading computing instructions (e.g., software, firmware, or the like), control parameters, patient data, or still other information to the PAP monitor 22, smart wearable 26, and smart device 28. In at least one case, control information from a user or a computing device will direct the PAP monitor 22 to determine when, if ever, a patient 12 dislodges a PAP mask 16.

In at least some cases, the logic module 42B and I/O module 44B of the smart wearable 26 are configured with at least a vibration device (e.g. a motor, a MEMs based actuator, or some other tactile human interface device (HID) structure). When the smart wearable 26 device receives a certain signal indicating that the patient 12 has dislodged his PAP mask 16, the logic module 42B will cause an alert to sufficiently inspire the patient 12 to re-form a seal of the PAP mask 16 to his air passage(s). In some cases, until the patient 12 re-establishes a suitable delivery of pressurized air via the PAP mask 16, the logic module 42B may be arranged to repeat, cycle, or otherwise continue the alert. The alert may be paused, snoozed, reset, or otherwise via automatic or manual actions of the patient 12. The logic module 42B may cause information representing the alert (e.g., time, duration, and the like) to be recorded. Other actions are of course contemplated.

The sleep apnea system 50 of FIG. 3 may be deployed by a sleep apnea patient 12 or the system may be directed for use by a medical practitioner. Since it can be very uncomfortable to use a PAP device, a medical practitioner will recognize that sleep apnea patients, especially new sleep apnea patients, frequently remove their masks in the middle of the night, often without being aware they are doing so. The sleep apnea patient in this case will typically miss out on the opportunity for a good night of sleep, and in at least some cases, the dislodged mask can also present a health risk.

Many PAP machines have an alarm to wake the patient when the air pressure in the system changes, but it is difficult or in some cases not possible to generate an alarm that will wake the patient without disturbing others who are sleeping. This problem is exacerbated when the PAP device 14 (FIGS. 1, 2) sets of the alarm several times per night. Hence, the existing alarms of many PAP devices 14 are not loud enough to wake up the sleep apnea patient 12 when the conditions to do so have been determined.

To resolve the problems of insufficient alarms in conventional PAP devices 14, a new PAP monitor 22 is now described. The PAP monitor 22 may be a mobile unit, a portable wall, a fixed unit, or formed in some other way. The PAP monitor 22 may be a wall-powered device, a battery powered device, or powered in some other way.

When the PAP monitor 22 is placed in proximity to the PAP device 14, the PAP monitor 22 will electronically listen and determine whether or not the PAP device 14 is making noise consistent with a regular breathing pattern of the patient 12. If the PAP monitor 22 detects, for example, that the patient 12 has been using the PAP mask 16 for at least a first period of time (e.g., two minutes, five minutes, fifteen minutes or some other time period), and then if the PAP monitor 22 detects, for example, that the patient 12 has stopped using the PAP mask 16 for at least a second period of time (e.g., 30 seconds, 60 seconds, two minutes, five minutes, or some other time period), then the PAP monitor will generate a particular alarm signal (e.g., a dislodged mask alert signal). The particular alarm signal will cause the smart wearable 26 (e.g., a wrist watch-like device, a bracelet, a pendant, an earring, a smart shirt, a smart headband, or some other smart wearable form factor) to output a signal to the patient 12. The output signal may be any one or more of a vibration, an audio signal, a visual signal, or some other output signal. In one case, the smart wearable is arranged as a bracelet or smart watch worn on the patient's wrist, leg, or another part of the body (e.g., FIG. 2B), which will vibrate rapidly to wake up the patient 12 until he places the PAP mask 16 back on his face. The output signal is directed only to the patient 12 and will not wake others who are not using the PAP device 14 (e.g., other people sleeping in the same room as the patient 12). In at least some embodiments, if the patient 12 successfully uses the PAP mask 16 for at least a third period of time or longer (e.g., four hours, seven hours, 9 hours, or some other time period), the PAP monitor 22 will reset, and the process starts all over again.

The inventor has recognized that any particular PAP device 14 will produce at least one audio signal having a group of frequencies produced by the air pumps of the PAP device 14. These air pump noises will be added to the audio signal (i.e., noise) produced when a breath is taken by the patient 12 and added to other ambient and transient noise in the general environment around the PAP device 14. Using this information, the inventor has further recognized that by analyzing a first default threshold level of sound (e.g., minimum sound) that is produced during a selected time window (e.g., sound over a two to four hour time period, sound over a one to five hour period, sound over a 60 minute time period, or some other time window), and then looking at the a second threshold level of sound (e.g., peak sound) during the same time window, then the breath of the patient 12 can be affirmatively detected. Next, by analyzing one or more differences between sound levels in the selected time window, then one or more "best" frequencies to detect the patient's breaths can be determined.

Figure 4:
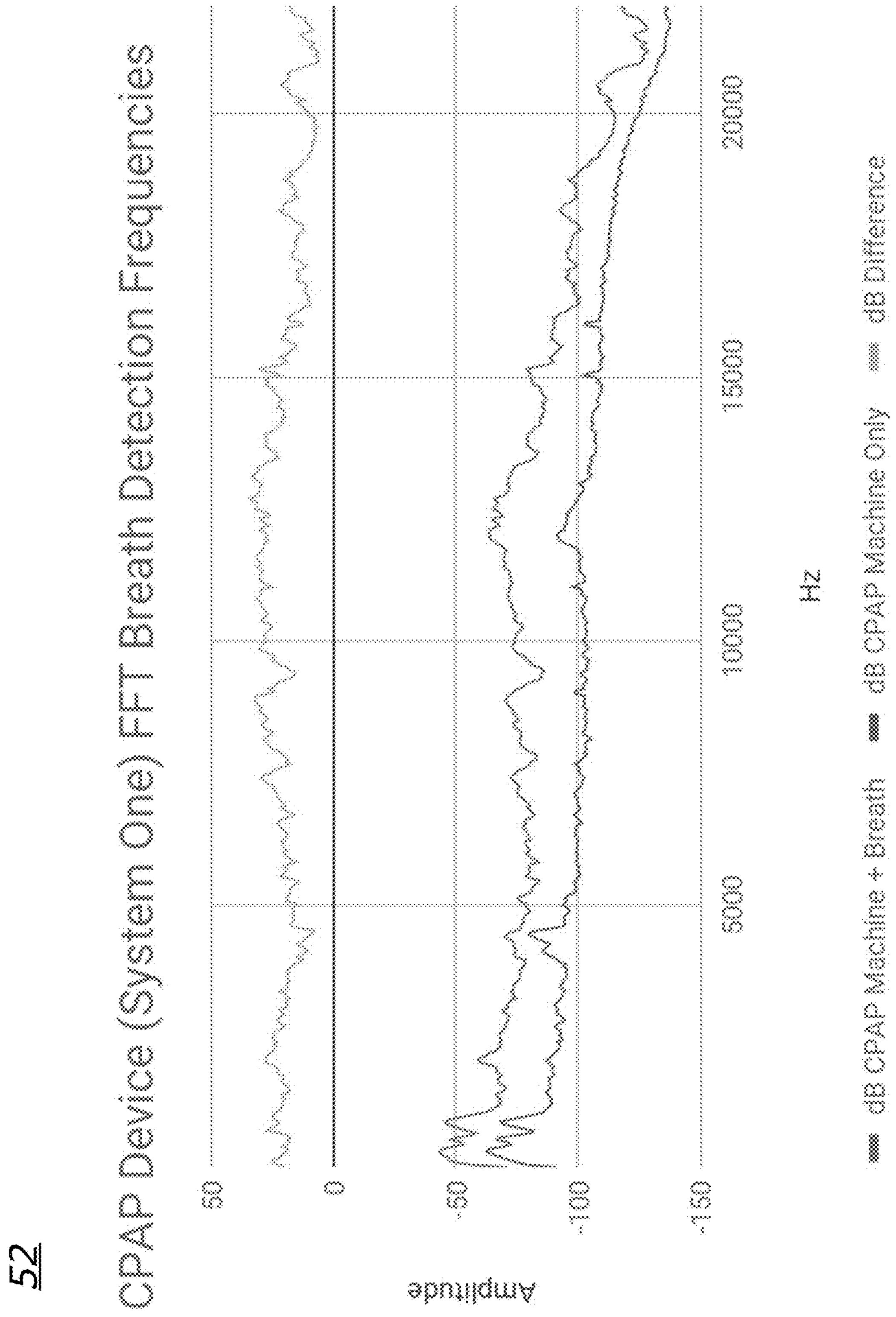
FIG. 4 is a frequency analysis graph mapping recorded noise from a PAP device, recorded noise from the PAP device and the patient, and a difference between the PAP device noise and PAP device plus patient noise.

FIG. 4 is a frequency analysis graph 54 mapping recorded noise from a PAP device 14, recorded noise from the PAP device 14 and the patient 12, and a difference between the PAP device noise and PAP device plus patient noise. In the frequency analysis graph 54, the horizontal axis represents frequency in Hertz (Hz), and the vertical axis represents signal amplitude in decibels (dB). The bottom (e.g., red) line shows maximum values for all of the frequencies from 0-25,000 Hz recorded when the PAP device 14 is running and there is not someone breathing; the middle (e.g., blue) line shows the minimum values for all of the frequencies from 0-25,000 Hz recorded when the PAP device 14 is running and the patient 12 is breathing; and the top (e.g., yellow) line shows the difference between the maximum and minimum values (i.e., the difference between the lowest graph line and the middle graph line).

By analyzing the third (i.e., top) line in frequency analysis graph 54, the "best" frequencies to use for each PAP device can be determined. In at least some cases, the top ten frequencies may be selected as "best" frequencies. These "best" frequencies in at least some cases are frequencies that have a strong audio signal, are repeated over time, are sufficiently distinguished from other frequencies, or are notable for some other characteristic. Stated differently, the "best" three to ten of frequencies may in some cases be selected to obtain a largest difference in sound between when the patient 12 is breathing regularly and when the patient 12 is either not breathing regularly or even not breathing at all.

The PAP monitor 22 described in the teaching herein draws data from a MEMs device (e.g., logic module 42A) arranged as a digital microphone. When detecting whether or not a patient has dislodged his PAP mask 16, the PAP monitor 22 will monitor and detect each breath of the patient. The captured microphone data will be analyzed to filter out other noise and focus on one or more specific frequencies produced by the PAP device 14 when the PAP device 14 is in use and when the patient 12 is properly wearing the PAP mask 16.

One robust way to determine that the PAP monitor 22 is detecting sound produced by properly wearing a PAP mask 16 is to isolate audio power peaks in a plurality (e.g., one to ten or some other number) of fast Fourier transform (FFT) frequency buckets. In at least one case, the sound captured by the digital microphone is processed using a 1024 bin FFT, and the average of three to ten buckets is used to help eliminate noise that is detected on the other buckets. Other numbers of FFT bins are contemplated, and other average numbers of buckets may be selected for any desirable reason. In at least one case, if it is determined that there is a difference of more than a determined percentile range (e.g., 10 percent, 20 percent, 40 percent or some other fractional or determined difference) between the selected number of buckets (e.g., three to ten buckets) and the average noise in the environment, then the sound is classified as a sound of proper PAP mask 16 usage. In at least some cases, the selected number of buckets (e.g., three to ten buckets) can be automatically selected by an analysis of the history of the FFT output for each selected time window of the previous night.

Figure 5:
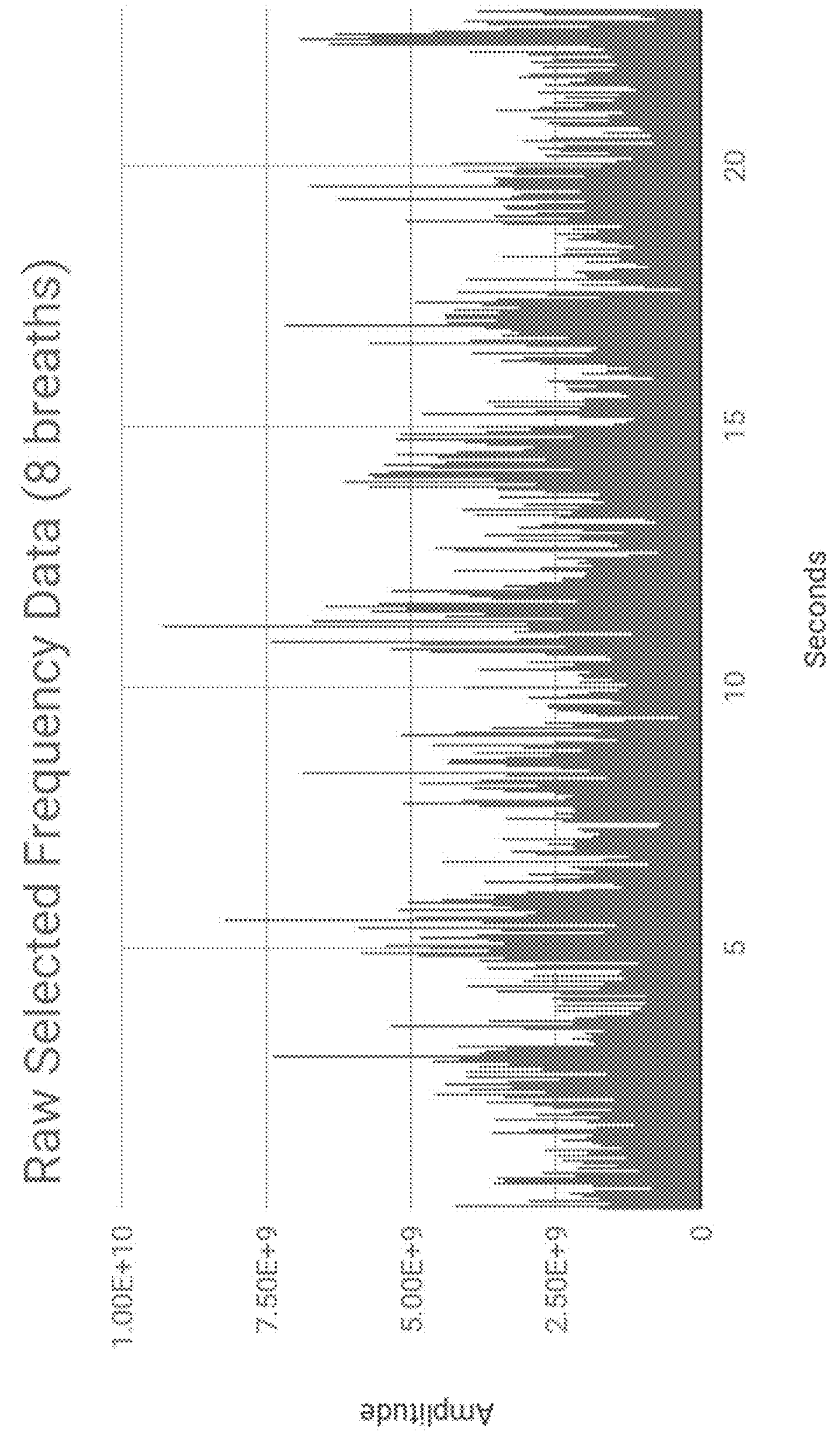
FIG. 5 is a sound amplitude graph showing amplitude data at one of the selected frequencies of interest.

FIG. 5 is a sound amplitude graph 54 showing amplitude data at one of the selected frequencies of interest. Audio data of the sound amplitude graph 54 is captured with the logic module 42A of the PAP monitor 22, and data is filtered according to the particular frequency analyzed. In the sound amplitude graph 54 of FIG. 5, the frequency of interest is 1600 Hz. The horizontal axis in the sound amplitude graph 54 represents time in seconds during which audio measurements were captured, and the vertical axis represents amplitude of the sound.

In the sound amplitude graph 54, a peak is determined by defining a lower FFT value on buckets adjacent to (i.e., buckets on either side of) the frequency bucket of interest. Because the audio frequency of interest could be exactly at a boundary of two buckets, the teaching of the present disclosure allows for an audio peak at a frequency of interest to be composed of two adjoining buckets wherein adjacent buckets on either side of the pair of interest have a lower audio signal. By identifying peaks having a greatest differential between one or three buckets, the "best" frequencies can be selected to identify when a patient 12 takes a breath. In the teaching herein, when peaks are identified or otherwise detected on at least three FFT buckets, then those buckets are, in at least some embodiments, set to be the default buckets. And using these identified buckets, the teaching of the present disclosure may capture sound during every sleep session and identify the breathing events of the sleep apnea patient 12. If the patient changes to a new PAP device 14, a new training session can be performed to identify a new set of "best" frequencies of interest.

Turning again to the sound amplitude graph 54 of FIG. 5, the graph shows the amplitude of recorded sound at 1600 Hz, which is one of the selected frequencies of interest for a particular PAP device 22. The data represented in FIG. 5 is raw data captured by the logic module 42A, which is arranged as a MEMs device digital microphone, over a period of 25 seconds. In the data of FIG. 5, eight breaths of the patient 12 are readily shown as peaks. As can also be seen from the raw data in FIG. 5, a large amount of noise is present, and this noise can be smoothed out.

Figure 6:
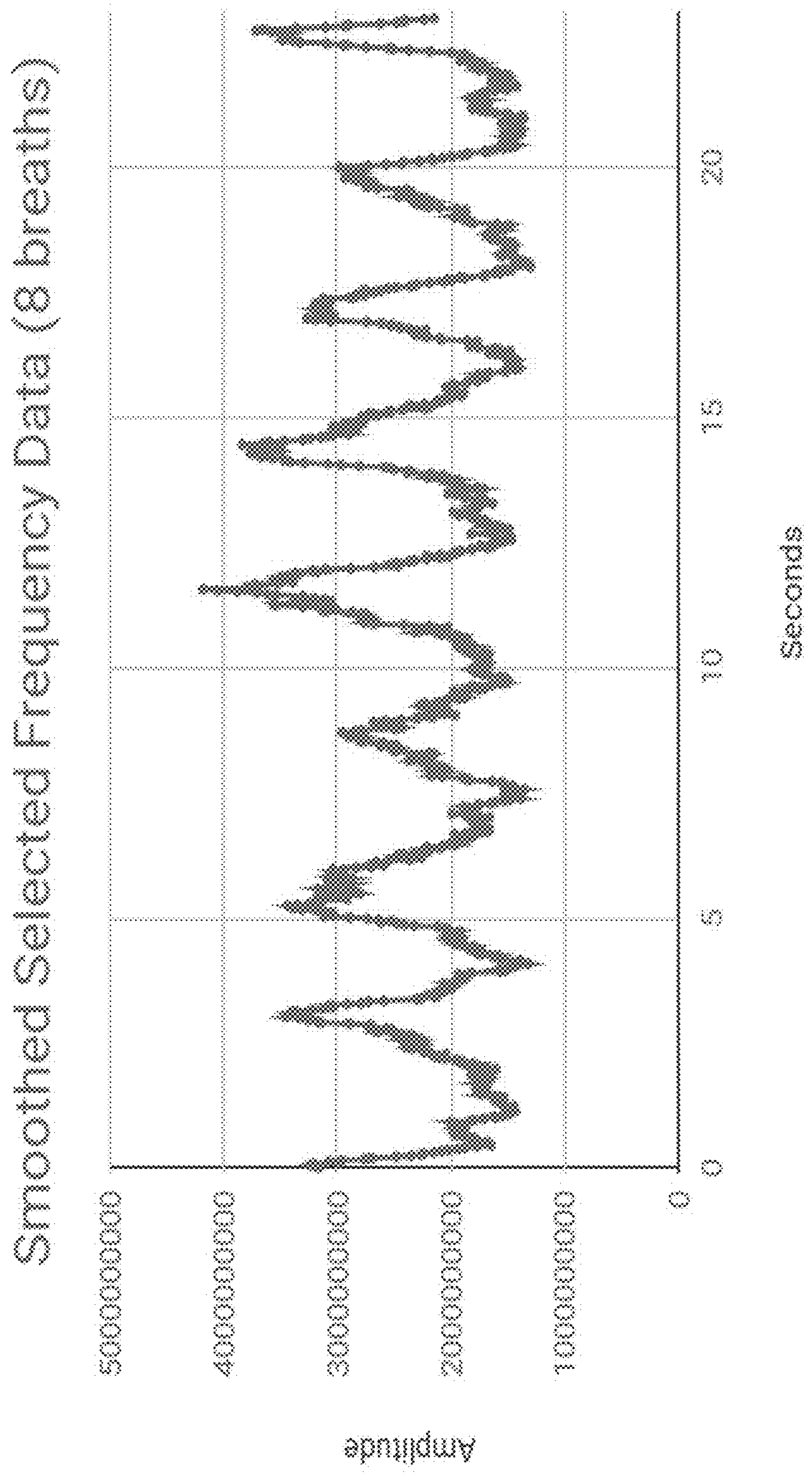
FIG. 6 is a smoothed amplitude graph showing the data of FIG. 5 after processing.

FIG. 6 is a smoothed amplitude graph 56 showing the data of FIG. 5 after processing. According to the teaching herein, a smoothing process includes each data point in a running average calculation. In at least some cases, a selected number of data points (e.g., 50 data points, 100 data points, 1000 data points, or some other number of data points) surrounding each data point of interest are summed. In these cases, the data point of interest may be centered in a window of the selected number of data points or the data point of interest may be weighted to one side or the other of the selected number of data points that are summed. Once summed, the final resultant sum may be divided by the selected number of data points to create an average value, which is then graphed along the lines of what is shown in FIG. 5. The smoothed amplitude graph 56 of FIG. 5 selects 100 data points surrounding each data point of interest for use in the averaging algorithm, and in this non-limiting case, the data point of interest is summed between the selected 100 data points; 50 on each side. In at least some cases, outlier data point, which may be determined by a selected one or more thresholds, may be eliminated and not used as either data points of interest or as data points in the summing function. Accordingly, when the present teaching includes the use of each collected data point, it is recognized that in some cases, data points determined to be non-useful may be excluded, and only determined useful, non-extreme data points are included.

The eight breaths of the patient 12, which are derived from the raw data sound amplitude graph 54 of FIG. 5, are even more clearly apparent in the smoothed amplitude graph 56 of FIG. 6. In the smoothed amplitude graph 56 of FIG. 6, a rising slope of each peak represents an inhalation event of the patient 12, and a falling slope of each peak represents an exhalation event of the patient 12.

Figure 7:
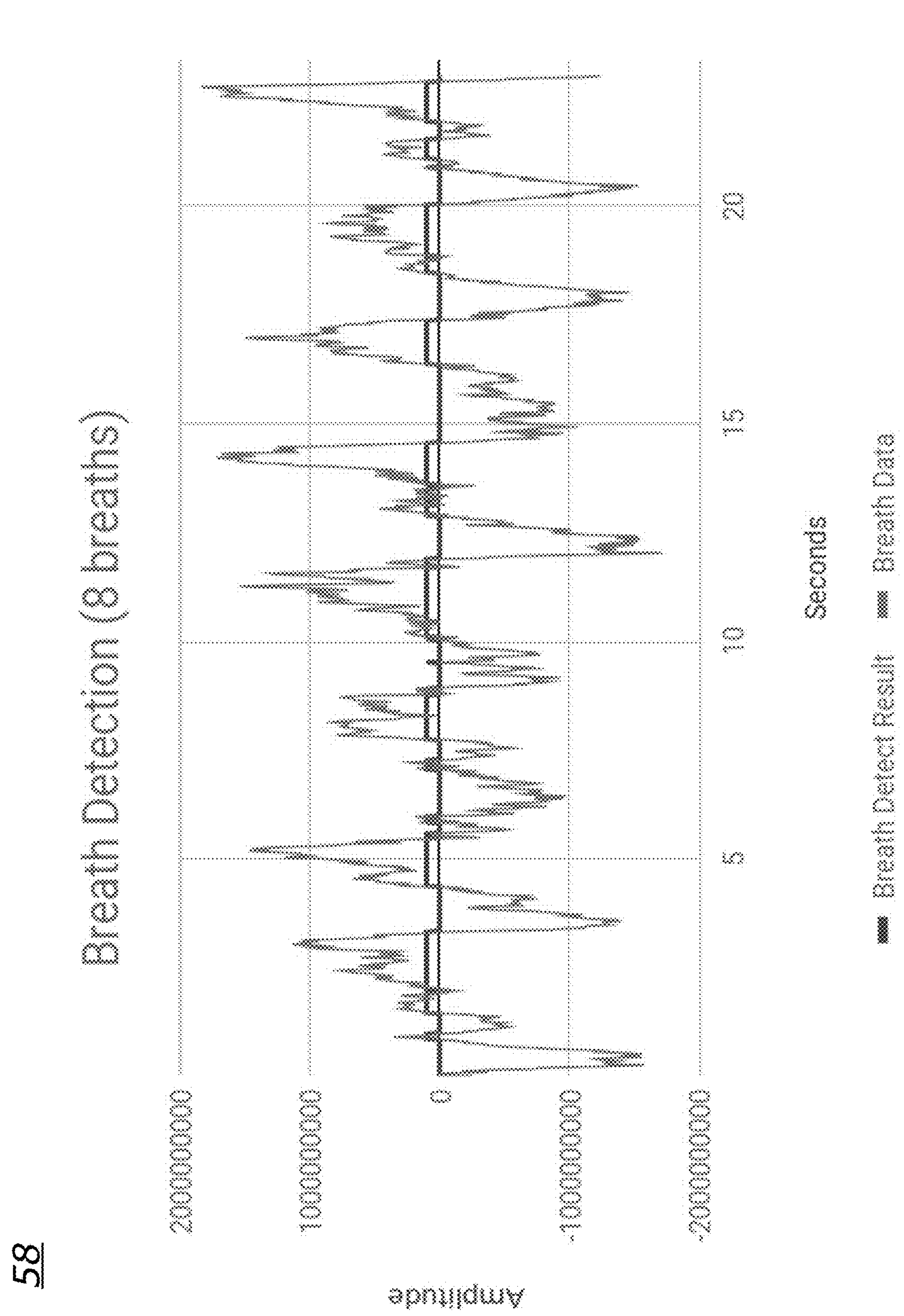
FIG. 7 is another amplitude graph 58 having alarm analysis threshold information superimposed thereon.

FIG. 7 is another amplitude graph 58 having alarm analysis threshold information superimposed thereon. The amplitude graph 58 uses smoothed data derived and recorded at a selected frequency over a 25 second window (horizontal axis) having clear amplitude (vertical axis) peaks representing breathing of the patient 12. Superimposed on the amplitude graph 58 is a line of connected "difference data" points. The difference data points are each an absolute value of peak amplitude value minus a corresponding trough points amplitude point, and each point is 250 miliiseconds apart from an adjacent point. The difference points are then connected together in sequence and set to a determined threshold value (e.g., 10 percent in FIG. 7, but many other selected thresholds are contemplated) of a determined (e.g., maximum) amplitude. The connected difference data points set to the threshold value form the superimposed threshold analysis.

Using the threshold values, the breaths of the patient can then be identified in one or more sets of clear binary decision points. For example, the threshold values can indicate if the patient 12 is or is not inhaling; the threshold values can indicate if the patient 12 is or is not exhaling; and the threshold values can indicate if the patient 12 has or has not stopped breathing. Additionally, each of these decision points may be analyzed in cooperation with a known point in time for any given breathing event.

In one exemplary embodiment of a practical application of the threshold data of FIG. 7, the PAP monitor 22 may detect each time a proper inhalation is taken by the patient 12. A proper inhalation is determined based on the sound of the PAP device 14 when the patient's PAP mask 16 is properly situated. In this case, upon each proper inhalation, a selected alarm timer will be reset (e.g., reset to zero or another initialization value). Then, if the alarm timer is not reset (i.e., if an expected proper inhalation does not occur) within a determined apnea time window (e.g., 30 seconds, 60 seconds, 90 seconds, or some other time), then the PAP monitor 22 will generate a dislodged mask alert signal. Based on the dislodged mask alert signal, an alarm signal will be communicated to the smart wearable 26, the smart device 28, or to some other computing device. The alarm signal may, for example, be sent between any one or more of transceivers 40A, 40B, 40C. The alarm signal may be continuously communicated, periodically communicated, communicated according to a user or programmatically selected schedule, or communicated in some other way. In at least some cases, one or both of the alarm signal and the dislodged mask alert signal may remain asserted until the patient re-seals the PAP mask 16 and a pattern of normal breathing by the patient 12 is reestablished.

In at least one other exemplary case, the PAP device 22 may be maintained in a standby or sleep state, and a determined snoring noise, filtered from amongst any other noises, may be detected. In this case, confirmation of the snoring may be used to awaken the PAP monitor 22 to begin an active monitoring of a sleep apnea condition caused by a dislodged PAP mask 16. Such embodiments may be useful for a mobile PAP monitor device 22 that has a transient power source such as a battery.

Figure 8:
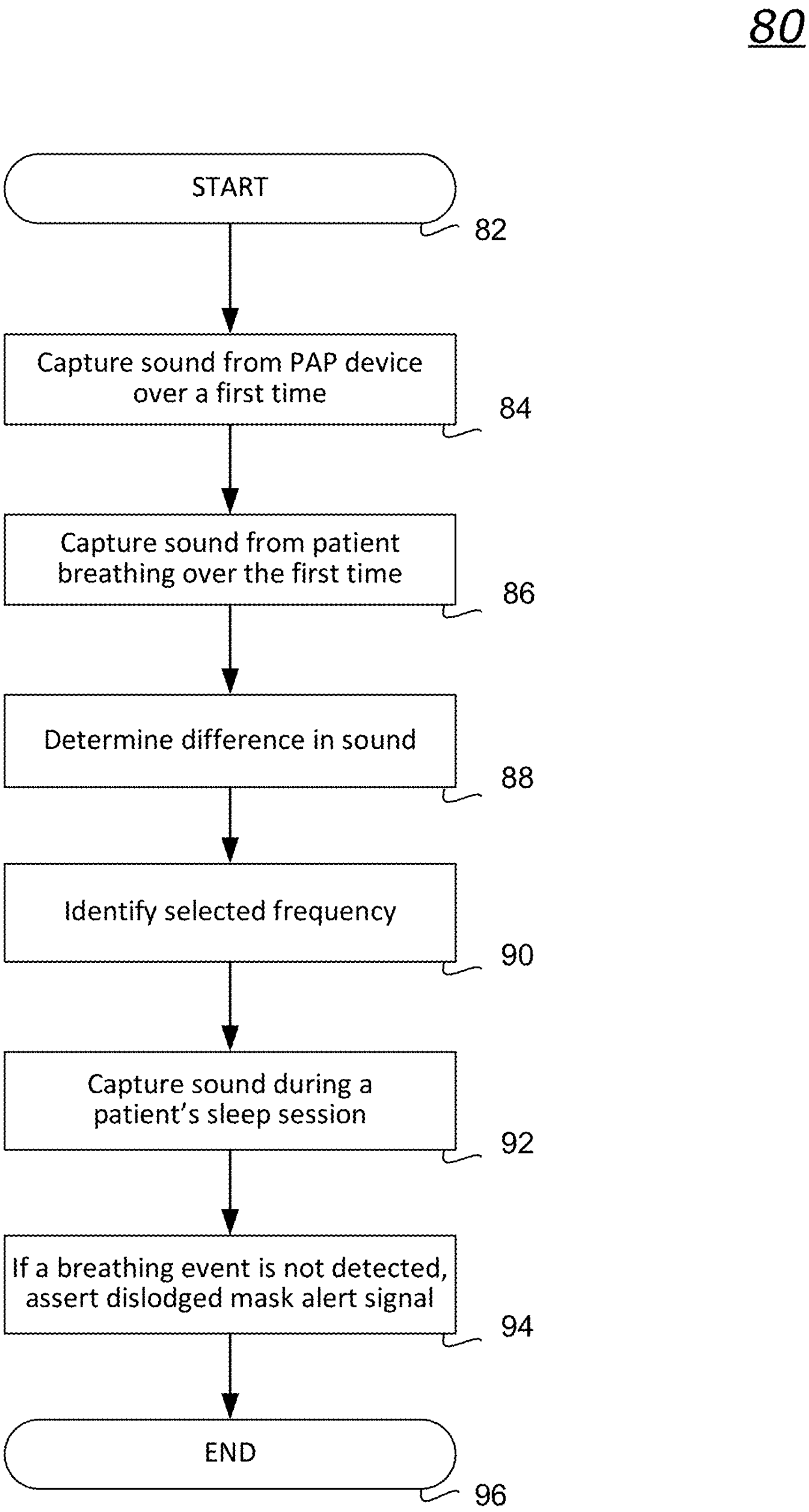
FIG. 8 is a data flow diagram representing a dislodged PAP mask detection process carried out with a PAP monitor system embodiment.

FIG. 8 is a data flow diagram representing a dislodged PAP mask detection process 80 carried out with a PAP monitor system embodiment such as the PAP monitor system monitor 50 of FIG. 3.

At 82, the procedure begins. A patient prepares to sleep with a positive airway pressure (PAP) device. The PAP device may be a CPAP device, an APAP device, a BIPAP device, or some other positive airway pressure device. The PAP device includes at least one airhose that is sealably coupled to a PAP mask, and the patient wears the mask over their nose, mouth, or nose and mouth. The PAP mask forms a seal against the skin of the patient so that the pressurized air provided by the PAP device does not escape. As the patient prepares to sleep and sleeps, pressurized air is provided to the patient to prevent sleep apnea events. Stated differently, the patient using the PAP device and its attachments is able to sleep through the night with regular breathing events and avoiding irregular breathing events, which are sleep apnea where the patient is prevented from breathing normally.

The PAP device includes one or more pumps, motors, or other such electromechanical structures, and in operation, the PAP device produces one or more detectable rhythmic sounds. In at least some cases, the PAP device will have one rhythmic sound when the patient's PAP mask is properly sealed and the patient is having regular breathing events, and in some cases, the PAP device will have a second sound when the PAP mask has been dislodged and the patient is having irregular breathing events.

After initialization processing at 82, processing works cooperatively at 84 and 86. At 84 and 86 respectively, sound from the PAP device is captured and sound from a patient breathing is captured during a first time period.

As the patient sleeps during the first time period, which may be deemed a test period, a calibration period, or some other time period, a PAP mask monitor is arranged to capture sounds of the PAP device, the patient breathing, and other ambient and episodic sounds. To this end, the PAP mask monitor device in some embodiments will have a microphone, a vibration detector, or some other logic device. In at least some cases, this logic device of the PAP mask monitor either is or includes one or more micro-electromechanical system (MEMs) devices, and the MEMs device is arranged as a microphone. In other embodiments, the MEMs device is a vibration detector arranged to collect data representing the sound produced during the patients sleep session (e.g., PAP device noise, patient breathing noise, ambient noise, and episodic noise). In still other cases, the logic module of the PAP mask monitor is arranged as a conventional microphone device.

As described in the teaching of the present disclosure, the PAP mask monitor will have at least a first processor, a first memory, a first micro-electromechanical system (MEMs) device, and a first transceiver. Other structures are included but not described for brevity. The PAP mask monitor via its first processor executing software instructions retrieved from the memory, will perform any number of practical applications to determine when a patient dislodges a PAP mask. In at least some cases, the PAP mask monitor device is a discrete device. In at least some other cases, the PAP mask monitor is arranged as a smart device such as a smart phone, a smart tablet, or some other smart device. In still other cases, the technology of the PAP mask monitor is integrated with, or otherwise configured in, a smart wearable device. In these and other cases, the smart wearable device may be arranged as at least one of a wrist-worn device, an ankle-worn device, a chest-worn device, a neck-worn device such as a pendant, an earring, a smart shirt, a smart headband, a shoulder based device, or some other body-worn device having computing device (i.e., smart) capabilities as taught in the present disclosure.

Using the microphone, vibration detector, or other such logic, the PAP mask monitor is arranged to capture data representing sound from the PAP device over the first period of time and capture data representing sound from the patient breathing over the first period of time.

In the processing at 84 and 86, the first time period may be any desirable time period. For example, the time period may be one hour, two hours, ten hours, or some other time duration. In some cases, the time duration may be the first portion of a patient's sleep session, and this first portion is re-analyzed every time the patient begins a sleep session (e.g., the first time period is re-analyzed every night). In at least some other cases, as data is being captured and analyzed during a sleep session to determine if the patient is properly wearing the PAP mask, the same data is concurrently or later used to re-calculate the frequency data used to determine a properly sealed mask placement during a next or other subsequent sleep session. After processing at 84 and 86, processing falls to 88 and 90.

At 88 and 90, the PAP mask monitor will identify peak noise, and the PAP mask monitor will distinguish regular breathing events of the patient from the rhythmic noise produced by the PAP device. The identification and distinguishing may be performed by analyzing a composite noise data signal with a fast Fourier transform (FFT) based analysis.

In a first portion of processing during the first time period, the PAP mask monitor will listen in a learning mode, which may be over two to four hours or over some different time period. In one embodiment, the PAP mask monitor will detect audio power peaks in one to ten FFT frequency buckets. Such processes may be conducted using 1024 bin FFT, or an FFT of any other suitable number of bins. Sound, as it is captured, is filtered by frequency into one of the frequency-based buckets. In at least some cases, an average of three to ten buckets is used to eliminate noise in other buckets. In such an embodiment, or in other embodiments, if a difference of twenty percent or more (i.e., >20%) is found between the three to ten buckets and the average PAP device noise, then the system will determine that PAP mask is being used properly. In at least some cases, the selection of the three to ten buckets is performed automatically based on data accumulated during the first time period (i.e., learning mode, training session, calibration, or other like term).

As part of the processing at 88, the PAP mask monitor will determine a difference between the PAP device sound and the patient breathing sound over the first period of time. And at 90, the PAP mask monitor will identify, based on a fast Fourier transform (FFT) analysis of the difference between the PAP device sound and the patient breathing sound over the first period of time, a selected frequency that can distinguish the patient's breathing from other noise. In some cases, the processing includes identifying, based on the fast Fourier transform (FFT) analysis of the difference between the PAP device sound and the patient breathing sound over the first period of time, a plurality of selected frequencies that can distinguish the patient's breathing from other noise, and based on an analysis of the sound at the selected plurality of frequencies captured during the sleep session of the patient, the processing includes identifying each of the plurality of breathing events of the patient.

In some cases at 88 and 90, processing may be summarized as including acts to listen for PAP air pump noise, acts to define peak sound values by having lower FFT values in buckets that are on either side of a bucket or group of adjacent buckets having a frequency of interest so assigned. In this case, for example, the PAP mask monitor processing will select a "best" frequency by detecting peaks with the greatest differential between one to three or more buckets. When peaks are detected on at least three FFT buckets, those buckets will be set as the default buckets (e.g., the default frequencies) used to distinguish PAP device noise from breathing event noise. Such calculations may occur once, twice, several times, or even every night. In at least some cases, the determination of frequencies and the "calibration" or "training" of the PAP mask monitor operations happen in background processing and are transparent to the patient. Further describing the processing of the PAP mask monitor in at least some cases, raw data representing sound is captured by a microphone at any number (e.g., 1024 or some other number) of the selected frequencies over the selected time period. Then, based on the raw data, patient breathing events (i.e., inhalations, exhalations, apnea events, and the like) are determined, counted, or processed in an different way.

After processing at 88 and 90, processing fall to 92 and 94 where data representing sound is captured during the patient's sleep session, and if an expected breathing event is not detected, then a dislodged mask alter signal is asserted and processed.

In at least some cases, processing at 92 and 94 includes capturing sound from the PAP device and from the patient breathing during the sleep session, and based on an analysis of the sound at the selected frequency captured during the sleep session of the patient, the PAP mask monitor will identify each of a plurality of breathing events of the patient. If a breathing event is not detected during a determined apnea time window, the PAP mask monitor will assert a dislodged mask alert signal.

In at least some other cases, the processing at 92 and 94 includes capturing sound from the PAP device and from the patient breathing during a sleep session, identifying each of a plurality of breathing events of the patient based on an analysis of the sound at the selected frequency captured during the sleep session, and assert a dislodged mask alert signal if a breathing event is not detected during a determined apnea time window; and The detection of breathing events in some cases includes distinguishing a regular breathing event from an irregular breathing event based on the analysis of the sound captured from the PAP device and from the patient breathing during the sleep session. In some cases, the determined apnea time window is between about 30 seconds and about 90 seconds, and in these or alternate cases, the determined apnea time window is about 60 seconds.

After the dislodged mask alert signal, an alarm signal is communicated to the smart wearable device. In cases where the PAP mask monitor is integrated into the smart wearable device, the alert signal may be the dislodged mask alert signal, and the alert signal may be processed internally. In other cases where the PAP mask monitor is a smart device or a discrete monitoring device, the assertion of the dislodged mask alert signal may cause transmission of the alert signal via a pair of communicatively coupled transceivers. The transceivers may comport with a BLUETOOTH protocol, a BLUETOOTH LOW ENERGY protocol, a WiFi (e.g., IEEE 801.11) protocol, or some other protocol. Receiving the alert signal at the smart wearable device will cause an output to be presented via a particular human interface device (HID) integrated with, or otherwise associated with, the smart wearable.

In some cases, the HID device is tactile vibration device. In some cases, the HID is audio output device. In these or still other cases, the HID device may also include a visual output device or some other interface device arranged to stir the patient from his sleep so that the PAP mask may be re-sealed against his skin and over his nose, mouth, or nose and mouth.

In some cases, the processing at 94 includes still other events based on distinguishing the patient's regular breathing events from irregular breathing events. For example, in some cases, the PAP mask monitor will wait for a determined delay period of time when a sleep session begins before asserting the dislodged mask alert signal. The determined delay period of time may be two minutes, five minutes, 30 minutes, or any other selected time period. In some cases, after the sleep session has continued for a sleep session duration time, which may be five hours, seven hours, ten hours, or any other selected time period, the system may reset and at least in some cases, suspend any assertion of the dislodged mask alert signal.

In some cases, the PAP mask monitor, after determining that the sleep apnea conditions exist or remain existing (e.g., irregular breathing events have been detected in accordance with the selected time periods), will assert the dislodged mask alert signal a single time until the conditions are corrected. In other cases, the dislodged mask alert signal will be continuously asserted, periodically asserted, asserted on a user or programmatically determined time period, or asserted according to some other condition. In some cases, the patient may be enabled to force a de-assertion of the dislodged mask alert signal, and in some other cases, the patient may be expressly prevented from de-asserting the dislodged mask alert signal except by correcting (i.e., re-sealing) the PAP mask.

For the avoidance of doubt, one of skill in the art will recognize that in the teaching of the present disclosure, time periods, actions, frequency selections, and other such control information and parameters may be initialized, changed, or otherwise controlled by a user via a user interface, via a programmatic interface, by manual intervention of a patient or medical practitioner, or via any other desired means.

After processing at 94, processing falls to 96.

Processing ends at 96.

Having now set forth certain embodiments, further clarification of certain terms used herein may be helpful to providing a more complete understanding of that which is considered inventive in the present disclosure.

In the teaching of present disclosure, one or more particular electronic structures of the PAP monitor 22, smart wearable 26, and smart device 28 are coupled, connected, or otherwise arranged in cooperation. The various components and devices of the embodiments are interchangeably described herein as "coupled," "connected," "attached," and the like. It is recognized that once assembled, the system is suitably arranged to perform the teaching described herein. The materials and the junctions formed at the point where two or more structures meet in the present embodiments are sealed to a mechanically, medically, or otherwise industrially acceptable level.

FIG. 8 includes a data flow diagram illustrating a non-limiting process that may be used by embodiments of a PAP monitor 22, smart wearable 26, and a smart device 28. In this regard, each described process may represent a module, segment, or portion of software code, which comprises one or more executable instructions for implementing the specified logical function(s). It should also be noted that in some implementations, the functions noted in the process may occur in a different order, may include additional functions, may occur concurrently, and/or may be omitted.

The figures in the present disclosure illustrate portions of one or more non-limiting computing device embodiments such as one or more components of the PAP monitor 22, smart wearable 26, and smart device 28. The computing devices may include operative hardware found in conventional computing device apparatuses such as one or more processors, volatile and non-volatile memory, serial and parallel input/output (I/O) circuitry compliant with various standards and protocols, wired and/or wireless networking circuitry (e.g., a communications transceiver), one or more user interface (UI) modules, logic, and other electronic circuitry.

Processing devices, or "processors," as described herein, include central processing units (CPU's), microcontrollers (MCU), digital signal processors (DSP), application specific integrated circuits (ASIC), peripheral interface controllers (PIC), state machines, and the like. Accordingly, a processor as described herein includes any device, system, or part thereof that controls at least one operation, and such a device may be implemented in hardware, firmware, or software, or some combination of at least two of the same. The functionality associated with any particular processor may be centralized or distributed, whether locally or remotely. Processors may interchangeably refer to any type of electronic control circuitry configured to execute programmed software instructions. The programmed instructions may be high-level software instructions, compiled software instructions, assembly-language software instructions, object code, binary code, micro-code, or the like. The programmed instructions may reside in internal or external memory or may be hard-coded as a state machine or set of control signals. According to methods and devices referenced herein, one or more embodiments describe software executable by the processor, which when executed, carries out one or more of the method acts.

As known by one skilled in the art, a computing device has one or more memories, and each memory comprises any combination of volatile and non-volatile computer-readable media for reading and writing. Volatile computer-readable media includes, for example, random access memory (RAM). Non-volatile computer-readable media includes, for example, read only memory (ROM), magnetic media such as a hard-disk, an optical disk, a flash memory device, a CD-ROM, and/or the like. In some cases, a particular memory is separated virtually or physically into separate areas, such as a first memory, a second memory, a third memory, etc. In these cases, it is understood that the different divisions of memory may be in different devices or embodied in a single memory. The memory in some cases is a non-transitory computer medium configured to store software instructions arranged to be executed by a processor. Some or all of the stored contents of a memory may include software instructions executable by a processing device to carry out one or more particular acts.

The computing devices illustrated herein (e.g., PAP monitor 22, smart wearable 26, smart device 28, and the like) may further include operative software found in a conventional computing device such as an operating system or task loop, software drivers to direct operations through I/O circuitry, networking circuitry, and other peripheral component circuitry. In addition, the computing devices may include operative application software such as network software for communicating with other computing devices, database software for building and maintaining databases, and task management software where appropriate for distributing the communication and/or operational workload amongst various processors. In some cases, the computing device is a single hardware machine having at least some of the hardware and software listed herein, and in other cases, the computing device is a networked collection of hardware and software machines working together in a server farm to execute the functions of one or more embodiments described herein. Some aspects of the conventional hardware and software of the computing device are not shown in the figures for simplicity.

Amongst other things, the exemplary computing devices of the present disclosure (e.g., PAP monitor 22, smart wearable 26, and smart device 28) may be configured in any type of mobile or stationary computing device such as a remote cloud computer, a computing server, a smartphone, a tablet, a laptop computer, a wearable device (e.g., eyeglasses, jacket, shirt, pants, socks, shoes, other clothing, hat, helmet, other headwear, wristwatch, bracelet, pendant, other jewelry), or the like. Accordingly, the computing devices include other components and circuitry that is not illustrated, such as, for example, a display, a network interface, memory, one or more central processors, camera interfaces, audio interfaces, and other input/output interfaces. In some cases, the exemplary computing devices may also be configured in a different type of computing device such as a headboard mounted multimedia device, an Internet-of-Things (IoT) device, a multimedia device, a motion detection device, or some other computing device.

When so arranged as described herein, each computing device may be transformed from a generic and unspecific computing device to a combination device arranged comprising hardware and software configured for a specific and particular purpose such as to provide a determined technical solution. When so arranged as described herein, to the extent that any of the inventive concepts described herein are found by a body of competent adjudication to be subsumed in an abstract idea, the ordered combination of elements and limitations are expressly presented to provide a requisite inventive concept by transforming the abstract idea into a tangible and concrete practical application of that abstract idea.

The embodiments described herein use computerized technology to improve the technology of sleep apnea PAP mask monitoring, but other techniques and tools remain available to determine if a patient's PAP mask has been dislodged. Therefore, the claimed subject matter does not foreclose the whole or even substantial dislodged PAP mask detection technological area. The innovation described herein uses both new and known building blocks combined in new and useful ways along with other structures and limitations to create something more than has heretofore been conventionally known. The embodiments improve on computing systems which, when un-programmed or differently programmed, cannot perform or provide the specific PAP mask monitoring features claimed herein. The embodiments described in the present disclosure improve upon known PAP mask monitoring processes and techniques. The computerized acts described in the embodiments herein are not purely conventional and are not well understood. Instead, the acts are new to the industry. Furthermore, the combination of acts as described in conjunction with the present embodiments provides new information, motivation, and business results that are not already present when the acts are considered separately. There is no prevailing, accepted definition for what constitutes an abstract idea. To the extent the concepts discussed in the present disclosure may be considered abstract, the claims present significantly more tangible, practical, and concrete applications of said allegedly abstract concepts. And said claims also improve previously known computer-based systems that perform PAP mask monitoring operations.

Software may include a fully executable software program, a simple configuration data file, a link to additional directions, or any combination of known software types. When a computing device updates software, the update may be small or large. For example, in some cases, a computing device downloads a small configuration data file as part of software, and in other cases, a computing device completely replaces most or all of the present software on itself or another computing device with a fresh version. In some cases, software, data, or software and data is encrypted, encoded, and/or otherwise compressed for reasons that include security, privacy, data transfer speed, data cost, or the like.

Database structures, if any are present in the PAP monitor 22, smart wearable 26, and smart device 28 described herein, may be formed in a single database or multiple databases. In some cases hardware or software storage repositories are shared amongst various functions of the particular system or systems to which they are associated. A database may be formed as part of a local system or local area network. Alternatively, or in addition, a database may be formed remotely, such as within a distributed "cloud" computing system, which would be accessible via a wide area network or some other network.

Input/output (I/O) circuitry, user interface (UI) modules, and transceivers as taught in the present disclosure may include serial ports, parallel ports, universal serial bus (USB) ports, IEEE 802.11 transceivers, BLUETOOTH and BLUETOOTH LOW ENERGY transceivers, and other transceivers compliant with protocols administered by one or more standard-setting bodies, displays, projectors, printers, keyboards, computer mice, microphones, micro-electromechanical (MEMS) devices such as accelerometers, and the like.

In at least one embodiment, devices such as the PAP monitor 22, smart wearable 26, and smart device 28 may communicate with each other and other computing devices via communication over a communications network 24. The communications network 24 may involve an Internet connection or some other type of local area network (LAN) or wide area network (WAN). Non-limiting examples of structures that enable or form parts of a network include, but are not limited to, an Ethernet, twisted pair Ethernet, digital subscriber loop (DSL) devices, wireless LAN, Wi-Fi, Worldwide Interoperability for Microwave Access (WiMax), or the like. The communications network 24 may alternatively or additionally involve a personal area network (PAN) that includes wired and wireless short range communications arranged according to any selected protocol such as BLUETOOTH, BLUETOOTH LOW ENERGY (BLE), IEEE 802.11 (WiFi), universal serial bus (USB), and the like.

In the present disclosure, memory may be used in one configuration or another. The memory may be configured to store data. In the alternative or in addition, the memory may be a non-transitory computer readable medium (CRM). The CRM is configured to store computing instructions executable by any one or more processors 36A, 36B, 36C of the PAP monitor 22, smart wearable 26, and smart device 28, respectively. The computing instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of a PAP monitor 22, smart wearable 26, and smart device 28 as the case may be.

Buttons, keypads, computer mice, memory cards, serial ports, bio-sensor readers, touch screens, and the like may individually or in cooperation be useful to a medical practitioner or patient operating the PAP monitor 22, smart wearable 26, and smart device 28. The devices may, for example, input control information into the system. Displays, printers, memory cards, LED indicators, temperature sensors, audio devices (e.g., speakers, piezo device, etc.), vibrators, and the like are all useful to present output information to the medical practitioner or patient operating the PAP monitor 22, smart wearable 26, and smart device 28. In some cases, the input and output devices are directly coupled to the PAP monitor 22, smart wearable 26, and smart device 28 and electronically coupled to a processor or other operative circuitry. In other cases, the input and output devices pass information via one or more communication ports (e.g., RS-232, RS-485, infrared, USB, etc.).

As described herein, for simplicity, a medical practitioner and a patient may in some cases be described in the context of the male gender. It is understood that a medical practitioner and a patient can be of any gender, and the terms "he," "his," and the like as used herein are to be interpreted broadly inclusive of all known gender definitions. As the context may require in this disclosure, except as the context may dictate otherwise, the singular shall mean the plural and vice versa; all pronouns shall mean and include the person, entity, firm or corporation to which they relate; and the masculine shall mean the feminine and vice versa.

The terms, "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds or milliseconds), and that the activity may be performed on an ongoing basis (e.g., receiving MEMs data, determining paused breathing events, determining a dislodged PAP mask, and the like). An example of an activity that is not real-time is one that occurs over an extended period of time (e.g., hours or days) or that occurs based on intervention or direction by a medical practitioner or patient or other activity.

In the absence of any specific clarification related to an express use in a particular context, where the terms "substantial" or "about" in any grammatical form are used as modifiers in the present disclosure and any appended claims (e.g., to modify a structure, a dimension, a time, a measurement, or some other characteristic), it is understood that the characteristic may vary by up to 30 percent. For example, a determined apnea time window may be described as covering about 60 seconds. In these cases, a PAP monitor 22, smart wearable 26, or smart device 28 that is formed having a determined apnea time window of exactly 60 seconds is implied. And though different from the exact precision of the term, the use of "about" to modify the characteristic permits a variance of the time window by up to 30 percent. Accordingly, a PAP monitor 22, smart wearable 26, or smart device 28 that is formed having a determined apnea time window particular linear dimension of 42 seconds is "about 60 seconds," and a PAP monitor 22, smart wearable 26, and smart device 28 that is formed having a determined apnea time window 78 seconds is also "about 60 seconds." In contrast, a PAP monitor 22, smart wearable 26, or smart device 28 that is formed having a determined apnea time window of 30 seconds or 90 seconds is not "about 60 seconds.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, the technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials is described herein.

In the present disclosure, when an element (e.g., component, circuit, device, apparatus, structure, layer, material, or the like) is referred to as being "On," "coupled to," or "connected to" another element, the elements can be directly on, directly coupled to, or directly connected to each other, or intervening elements may be present. In contrast, when an element is referred to as being "directly on," "directly coupled to," or "directly connected to" another element, there are no intervening elements present.

The terms "include" and "comprise" as well as derivatives and variations thereof, in all of their syntactic contexts, are to be construed without limitation in an open, inclusive sense, (e.g., "including, but not limited to"). The term "or," is inclusive, meaning and/or. The phrases "associated with" and "associated therewith," as well as derivatives thereof, can be understood as meaning to include, be included within, interconnect with, contain, be contained within, connect to or with, couple to or with, be communicable with, cooperate with, interleave, juxtapose, be proximate to, be bound to or with, have, have a property of, or the like.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the present disclosure, the terms first, second, etc., may be used to describe various elements, however, these elements are not to be limited by these terms unless the context clearly requires such limitation. These terms are only used to distinguish one element from another. For example, a first machine could be termed a second machine, and, similarly, a second machine could be termed a first machine, without departing from the scope of the inventive concept.

The singular forms "a," "an," and "the" in the present disclosure include plural referents unless the content and context clearly dictates otherwise. The conjunctive terms, "and" and "or" are generally employed in the broadest sense to include "and/or" unless the content and context clearly dictates inclusivity or exclusivity as the case may be. The composition of "and" and "or" when recited herein as "and/or" encompasses an embodiment that includes all of the elements associated thereto and at least one more alternative embodiment that includes fewer than all of the elements associated thereto.

In the present disclosure, conjunctive lists make use of a comma, which may be known as an Oxford comma, a Harvard comma, a serial comma, or another like term. Such lists are intended to connect words, clauses or sentences such that the thing following the comma is also included in the list.

The headings and Abstract of the Disclosure provided herein are for convenience only and do not interpret the scope or meaning of the embodiments.

The teaching of a PAP monitor 22, smart wearable 26, and smart device 28 in the present disclosure provides several technical effects and advances to the field of PAP mask monitoring.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method to monitor a positive airway pressure (PAP) mask, comprising:

capturing sound from a positive airway pressure (PAP) device over a first period of time;

capturing sound from a patient breathing over the first period of time;

determining a difference between the PAP device sound and the patient breathing sound over the first period of time;

identifying, based on a fast Fourier transform (FFT) analysis of the difference between the PAP device sound and the patient breathing sound over the first period of time, a selected frequency that can distinguish the patient's breathing from other noise;

capturing sound from the PAP device and from the patient breathing during a sleep session;

based on an analysis of the sound at the selected frequency captured during the sleep session of the patient, identifying each of a plurality of breathing events of the patient; and if a breathing event is not detected during a determined apnea time window, asserting a dislodged mask alert signal.

2. The method of claim 1, wherein the sound captured during the first period of time is a training session that occurs prior to the sleep session.

3. The method of claim 1, wherein the determined apnea time window is about 60 seconds.

4. The method of claim 1, wherein the determined apnea time window is between about 30 seconds and about 90 seconds.

5. The method of claim 1, wherein detecting the breathing event includes distinguishing a regular breathing event from an irregular breathing event based on the analysis of the sound captured from the PAP device and from the patient breathing during the sleep session.

6. The method of claim 1, comprising:

identifying, based on the fast Fourier transform (FFT) analysis of the difference between the PAP device sound and the patient breathing sound over the first period of time, a plurality of selected frequencies that can distinguish the patient's breathing from other noise; and based on an analysis of the sound at the selected plurality of frequencies captured during the sleep session of the patient, identifying each of the plurality of breathing events of the patient.

7. The method of claim 1, comprising:

delaying the asserting of the dislodged mask alert signal for a least a first time period during a start of the sleep session until a determined number of breathing events are identified.

8. The method of claim 1, comprising:

based on asserting the dislodged mask alert signal, causing an alarm signal to be triggered at a smart wearable device being worn by the patient.

9. The method of claim 8, wherein the smart wearable device is at least one of a wrist-worn device, a pendant, an earring, a smart shirt, or a smart headband.

10. The method of claim 8, wherein the alarm signal triggered at the smart wearable device causes a tactile event.

11. A system, comprising:

a positive airway pressure (PAP) mask monitor having a first processor, a first memory, a first micro-electromechanical system (MEMs) device, and a first transceiver; and a smart wearable device, having a second processor, a second memory, a logic module, and a second transceiver, wherein the PAP mask monitor first processor, when executing instructions retrieved from the first memory, is configured to:

capture, with the MEMs device, sound from a PAP device over a first period of time;

capture, with the MEMs device, sound from a patient breathing over the first period of time;

determine a difference between the PAP device sound and the patient breathing sound over the first period of time;

identify, based on a fast Fourier transform (FFT) analysis of the difference between the PAP device sound and the patient breathing sound over the first period of time, a selected frequency that can distinguish the patient's breathing from other noise;

capture sound from the PAP device and from the patient breathing during a sleep session;

identify each of a plurality of breathing events of the patient based on an analysis of the sound at the selected frequency captured during the sleep session;

assert a dislodged mask alert signal if a breathing event is not detected during a determined apnea time window; and communicate an alarm signal via the first transceiver to the smart wearable device; and wherein the smart wearable device second processor, when executing instructions retrieved from the second memory, is configured to:

receive the alarm signal via the second transceiver; and assert an output via the logic module.

12. The system of claim 11, wherein the first transceiver and the second transceiver operate according to a BLUETOOTH LOW ENERGY protocol.

13. The system of claim 11, wherein the smart wearable device is at least one of a wrist worn device, a pendant, an earring, a smart shirt, or a smart headband.

14. The system of claim 11, wherein the PAP mask monitor is a smartphone.

15. The system of claim 11, wherein the PAP mask monitor is built into a PAP device that is arranged to provide a supply of pressurized air to a PAP mask.

16. The system of claim 11, wherein the PAP mask monitor first processor, when executing instructions retrieved from the first memory, is further configured to:

identify additional breathing events of the patient after the dislodged mask alert signal has been asserted; and de-assert the dislodged mask alert signal.

17. A system, comprising:

a PAP device arranged to provide a supply of pressurized air to a PAP mask, the PAP device having a first processor, a first memory, and a first transceiver;

a positive airway pressure (PAP) mask monitor built into the PAP device; and a smart wearable device, having a second processor, a second memory, a logic module, and a second transceiver, wherein the PAP mask monitor, via the first processor executing instructions retrieved from the first memory, is configured to:

receive data from at least one sensor associated with the PAP mask;

determine that the PAP mask has been dislodged;

based on the determination that the PAP mask is dislodged, assert a dislodged mask alert signal; and communicate an alarm signal via the first transceiver to the smart wearable device; and wherein the smart wearable device second processor, when executing instructions retrieved from the second memory, is configured to:

receive the alarm signal via the second transceiver; and assert an output via the logic module.

18. The system of claim 17, wherein output asserted via the logic module of the smart wearable device is a tactile output.

* * * * *